United States Patent [19]
Taki et al.

[11] Patent Number: 5,800,426
[45] Date of Patent: Sep. 1, 1998

[54] HIGH-FREQUENCY HEATING POWER DEVICE FOR CATHETER

[75] Inventors: Waro Taki, Osaka; Akiyo Sadato, Kyoto; Atsushi Ogawa, Kanagawa; Yasuhiro Goto; Shinichi Hirano, both of Aichi, all of Japan

[73] Assignees: Kabushiki Kaisha Tokai Rika Denki Seisakush., Niwa-gun; Kaneka Medix Corporation, Osaka, both of Japan

[21] Appl. No.: 648,882

[22] Filed: May 16, 1996

[30] Foreign Application Priority Data

May 19, 1995 [JP] Japan ................................. 7-121162

[51] Int. Cl.⁶ .................................................. A61B 17/38
[52] U.S. Cl. ..................... 606/32; 606/41; 606/35; 606/108
[58] Field of Search ............................. 606/28, 29, 32, 606/34, 35, 40, 41, 42, 191, 1, 108; 123/1, 12; 604/104

[56] References Cited

U.S. PATENT DOCUMENTS

| | | | |
|---|---|---|---|
| 5,078,714 | 1/1992 | Katims | 606/32 |
| 5,354,295 | 10/1994 | Guglielmi et al. | 606/32 |
| 5,569,245 | 10/1996 | Guglielmi et al. | 606/32 |
| 5,599,346 | 2/1997 | Edwards et al. | 606/41 |
| 5,624,449 | 4/1997 | Phan et al. | 606/32 |
| 5,643,254 | 7/1997 | Scheldrup et al. | 606/32 |

FOREIGN PATENT DOCUMENTS

| | | |
|---|---|---|
| 4-10831 | 2/1992 | Japan . |
| 5-500322 | 1/1993 | Japan . |
| 7-265431 | 10/1995 | Japan . |

*Primary Examiner*—Jennifer Bahr
*Assistant Examiner*—Bryan K. Yarnell
*Attorney, Agent, or Firm*—Morgan, Lewis & Bockius LLP

[57] ABSTRACT

A high frequency heating power device for an implanted device comprises a switch circuit, an input/output circuit, a high-frequency signal generating circuit, and a check circuit. When a high frequency output circuit applies a high frequency measuring voltage between a guide wire and the body ground board, a voltage is detected which corresponds to the impedance of a circuit which is made up of lead wires, the guide wire, the patient's body, and the body grounding board. It is determined by a discriminating circuit whether or not the voltage thus detected is in a predetermined allowable voltage range. The operator is informed of the discrimination by means of a display circuit and a buzzer circuit, so that he can determine the position of the end of the guide wire with respect to the end of the catheter with ease.

13 Claims, 5 Drawing Sheets

APPROXIMATELY 1 mm

HIGH-FREQUENCY HEATING POWER DEVICE FOR CATHETER

BACKGROUND OF THE INVENTION

1. Field of the Invention

This invention relates to a high-frequency power unit for a member detained in a patient's body (hereinafter referred to as "an implanted device", when applicable) which supplies a high-frequency voltage to separate an a implanted device from an electrode thereby to cause it to stay in the affected part of a blood vessel.

2. Related Art

In the case of the affected part of a blood vessel, where for instance a cerebral aneurysm is formed, the following embolic medical treatment is employed: That is, an implanted device is inserted into the cerebral aneurysm, and a thrombus is formed with the affected part as the center.

In order to practice the above-described method, the following equipment is employed:

An implanted device is connected through a joint member, which is thermally molten, is connected to the end of a guide wire (or electrode). The guide wire is inserted into a catheter, and then led into the blood vessels from the femoral artery to the cranial artery. Under this condition, the implanted device is moved to the cerebral aneurysm while visually watching the fluoroscopic image formed by an X-ray radiographing unit. In order to determine whether or not the position of the end of the guide wire with respect to the end of the catheter is suitable for fusing the joint member, radiopaque markers are provided near the end of the guide wire and near the end of the catheter. For instance, in the case where the radiopaque marker on the guide wire is located between two radiopaque markers on the catheter which are spaced a predetermined distance from each other, a high-frequency power unit is operated to apply a high-frequency voltage to the base part of the guide wire from outside to fuse the joint member, thereby to detach the implanted device from the guide wire. With the implanted device left in the cerebral aneurysm, the catheter, together with the guide wire, is removed from the blood vessels and the operation is ended.

The implanted device is in the form of a coil made of a conductive metal material such as platinum which does not affect the patient's body. The material is extremely flexible so that it can be readily moved through the blood vessels to the targeted aneurysm.

With the above-described conventional equipment, in order to detach the implanted device from the guide wire, the position of the guide wire is confirmed while watching the fluoroscopic image formed by the X-ray radiographing unit. Hence, in the case where the X-ray radiographing unit is low in performance, or the radiopaque markers on the guide wire and the catheter are hidden by an image-forming object or objects such as other embolic materials, it is difficult to determine whether or not the position of the guide wire is suitable for fusing the joint member. Under these conditions, the operation takes a long time, thus placing an additional physical burden on the patient.

SUMMARY OF THE INVENTION

In view of the foregoing, an object of the invention is to provide a high-frequency heating power unit with which the position of the electrode at the point where the implanted device is to be detached from the latter can be confirmed without reference to the fluoroscopic image formed by the X-ray radiographing unit.

The foregoing object of the invention has been achieved by the provision of a power unit which applies a voltage through lead wires between an electrically conductive electrode which is inserted into a catheter and a grounding plate which is set in contact with a patient's body, to heat the end of the electrode; which, according to the invention, comprises:

impedance measuring means which applies a high frequency measuring voltage lower than the voltage between the electrode and the grounding plate, to measure an impedance of a circuit which is made up of the lead wires, the electrode, the patient's body, and the grounding plate.

In the power unit, a implanted device is connected through a joint member to the end of the electrode, and the joint member further may be fused by the application of a.

The power unit may comprise comparison means which determines whether or not an impedance value measured by the impedance measuring means is in a predetermined allowable range, and outputs a signal when the impedance value is out of the predetermined allowable range.

Furthermore, the power unit may further comprise: informing means which is operated according to a signal provided by the comparison means.

Moreover, the power unit comprises: inhibiting means which, when an impedance value measured by the impedance measuring means is out of the predetermined allowable range, inhibits the application of the voltage which is used for fusing the joint member.

With the power unit of the present invention, application of the high-frequency measuring voltage between the electrode and the grounding plate through the lead wires causes a current to flow between the electrode and the grounding plate through the electrolytes of the patient's body. During this procedure, the impedance measuring means is operated to measure the impedance of the circuit which consists of the lead wires, the electrode, the patient's body and the grounding plate. The impedance depends on the contact of the electrode with the electrolytes of the patient's body.

For instance, in the case where the end of the electrode is located inside the catheter, the amount of electrolytes allowed to enter the catheter is extremely small, and therefore current scarcely flows between the electrode and the grounding plate. The electrode and the grounding plate are substantially electrically insulated from each other, in other words, the impedance is considerably high. On the other hand, in the case where the end of the electrode, is located outside the catheter, even slightly, the end of the electrode is brought into direct contact with the electrolytes the patient's body, and therefore current readily flows between the electrode and the grounding plate.

In this case, the impedance is lower than that which is measured in the above-described case in which the electrode is located inside the catheter. As the end of the electrode exits the catheter, the contact area of the electrode with the electrolytes of the patient's body is increased, and current more readily flows between the electrode and the grounding plate. As the end portion of the electrode, which is outside the catheter, is increased in length, the impedance is decreased. Therefore, the position of the end of the electrode can be determined from the impedance value measured with the impedance measuring means.

Hence, even in the following case, the fusing position of the implanted device can be readily determined. Even in the case where the fluoroscopic image formed by the X-ray radiopaque unit is poor (not clear), or even in the case where, depending on the position where the implanted device is to be led, the end of the electrode is hidden by an image-forming object, such as an embolic material, and therefore it is impossible to locate the end of the electrode with respect to the end of the catheter through the X-ray fluoroscopic image, the fusing position of the implanted device can be readily confirmed from the impedance value measured with the impedance measuring means.

As was described before, the high-frequency measuring voltage is lower than the voltage. Hence, the joint member will never be fused during the measurement of the impedance.

The power unit of the present invention, the impedance measuring means measures the impedance of the circuit comprising the lead wires, the electrode, the patient's body. The grounding plate, and the comparison means determines whether or not the impedance measured is in the predetermined allowable range. In order to fuse the joint member to detach the implanted device from the electrode, the end of the electrode should slightly protrude from the end of the catheter—it should be set at the best position. In this case the allowable range of impedances of the circuit is determined, with the upper and lower limit values being set. Hence, it can be determined by the comparison means whether or not the impedance value of the circuit is in the predetermined allowable range. When it is determined that the impedance value is in the predetermined allowable range, the comparison means outputs a signal and in response to the signal from the comparison means, an operation for detachment of the implanted device can be suitably achieved.

If the impedance value of the circuit, measured with the impedance measuring means, is out of the predetermined allowable range the comparison means outputs another signal. Hence, it can be determined by signal produced whether it is impossible (not permitted) to detach the implanted device, and in this case the appropriate operation is taken.

The power unit of the present invention, in response to the signal from the comparison means, the informing means is operated and detects with ease whether or not the impedance of the circuit is in the predetermined allowable range. In other words, it can be visually or auditorily determined without reference to the fluoroscopic image formed by the X-ray radiopaque unit whether the electrode is at the position suitable for detachment of the implanted device.

With the power unit of the present invention, when the impedance value measured by the impedance measuring means is out of the predetermined allowable range, the inhibiting means inhibits the application of the voltage, so that the joint member is not fused. This eliminates the difficulty that the joint member is fused by mistake when the position of the end of the electrode with respect to the end of the catheter is not suitable for detachment of the implanted device.

DETAILED DESCRIPTION OF THE PREFERRED EMBODIMENTS

One preferred embodiment of the invention will be described with reference to the accompanying drawings.

Figure 2:
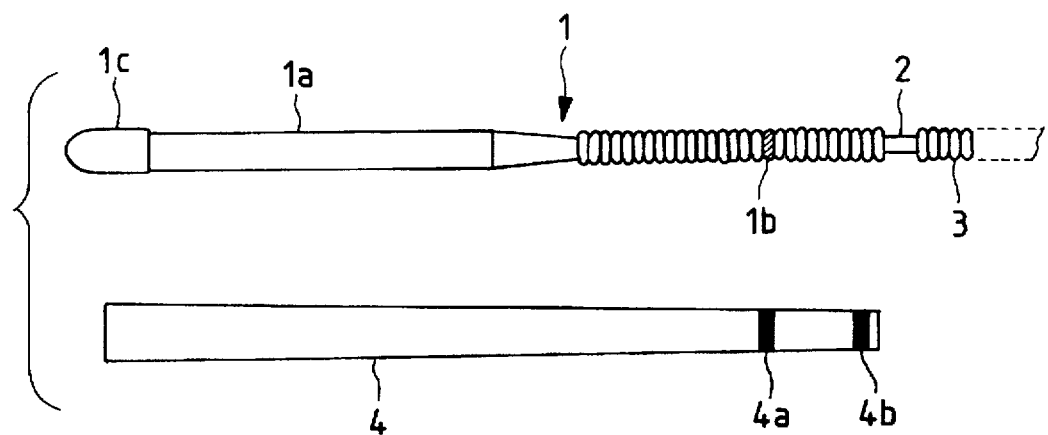
FIG. 2 is a side view showing a guide wire and a catheter.

In FIG. 2, reference numeral 1 designates a guide wire which is made of stainless steel which is electrically conductive. One end portion of the guide wire 1 is connected to a coil-shaped implanted device 3 through a joint member 2 which is made of thermally fusible connecting material such as polyvinyl alcohol (PVA). The implanted device 3 is in the form of a dual coil which is made of electrical conductive metal material such as platinum which does not adversely affect the patient's body. The guide wire 1 is inserted into a catheter 4, and then inserted into the blood vessels from a predetermined point on the patient's body. The implanted device 3 is led to the affected area while watching the X-ray fluoroscopic image. In this case, the above-describe operation is carried out with a Teflon® coated grip 1a gripped.

Figure 3:
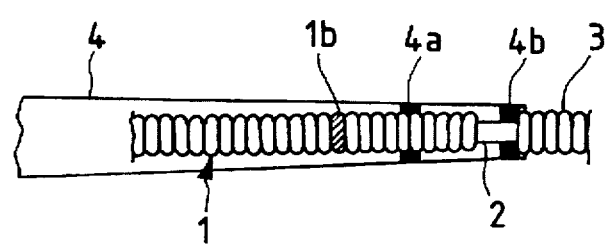
FIG. 3 is a diagram showing the case where a joint member is located inside the catheter.

That is, the guide wire 1 has a radiopaque marker 1b near its end, while the catheter 4 has radiopaque marks 4a and 4b near its end. While watching the X-ray fluoroscopic image, as shown in FIGS. 3, 4 and 5, the position of the one radiopaque marker 1b of the guide wire 1 and those of the two radiopaque markers 4a and 4b of he catheter 4 are visually detected to determine whether or not the end of the guide wire 1 is inside the catheter 4.

Figure 4:
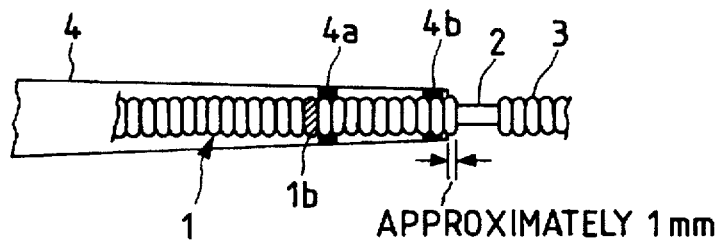
FIG. 4 is a diagram showing the case where the joint member is slightly protruded from the end of the catheter.
Figure 5:
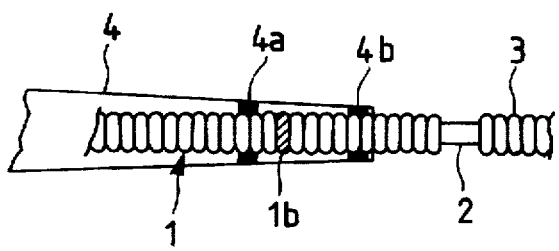
FIG. 5 is a diagram showing the case the joint member is protruded from the end of the catheter.

In detaching the implanted device 3 from the guide wire which has been inserted into the affected area, it is preferable that the end of the joint member 2 is substantially in alignment with the end of the catheter 4, or it is about 1 mm outside of it (as shown in FIG. 4). In the case where the end of the joint member 2 is located substantially outside of the catheter 4 (as shown in FIG. 5), or in the case where the end of the joint member 2 is located greatly out of the catheter 2 (as shown in FIG. 3), it is impossible to leave the implanted device 3 in the targeted affected area. For instance, in the case of FIG. 3 the joint member 2 can be fused off, however, sometimes it is impossible to detach the implanted device 3 from the catheter 4. In the case of FIG. 5, it is impossible sometimes to fuse the joint member 2.

Figure 6:
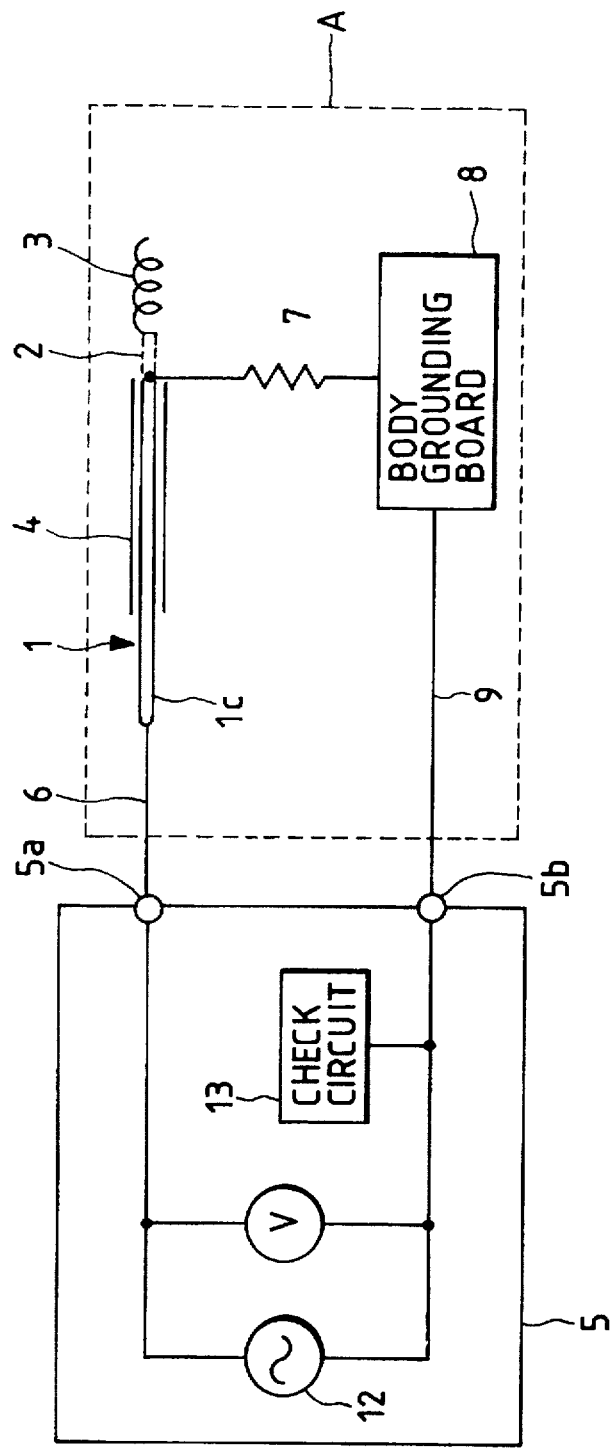
FIG. 6 is a circuit diagram, partly as a block diagram, showing the power unit which is coupled to a patient's body.

In order to detach the implanted device 3, which has been led to the affected area, by the guide wire, a high-frequency fusing voltage is applied to the guide wire 1 which is a high-frequency heating voltage, to fuse the joint member located between the implanted device 3 and the guide wire 1. More specifically, as shown in FIG. 6, the base portion of the guide wire 1, namely, an electrode connecting portion 1c is connected through a lead wire 6 to one output terminal 5a of a high-frequency heating power unit 5, while a grounding plate, namely, a body grounding board 8 is connected to through a lead wire 9 to the other output terminal 5b, so that a high-frequency fusing voltage is supplied between the guide wire 1 and the body grounding board 8. Furthermore, the power unit 5 applies a high-frequency measuring voltage between the guide wire 1 and the body grounding board 8 which is lower than the high-frequency fusing voltage, to detect a current which flows in a circuit which is made up of the lead wire 6, the guide wire 1, the patient's body 7, the body grounding board 8, and the lead wire 9, to determine the location of the end of the guide wire 1.

Figure 1:
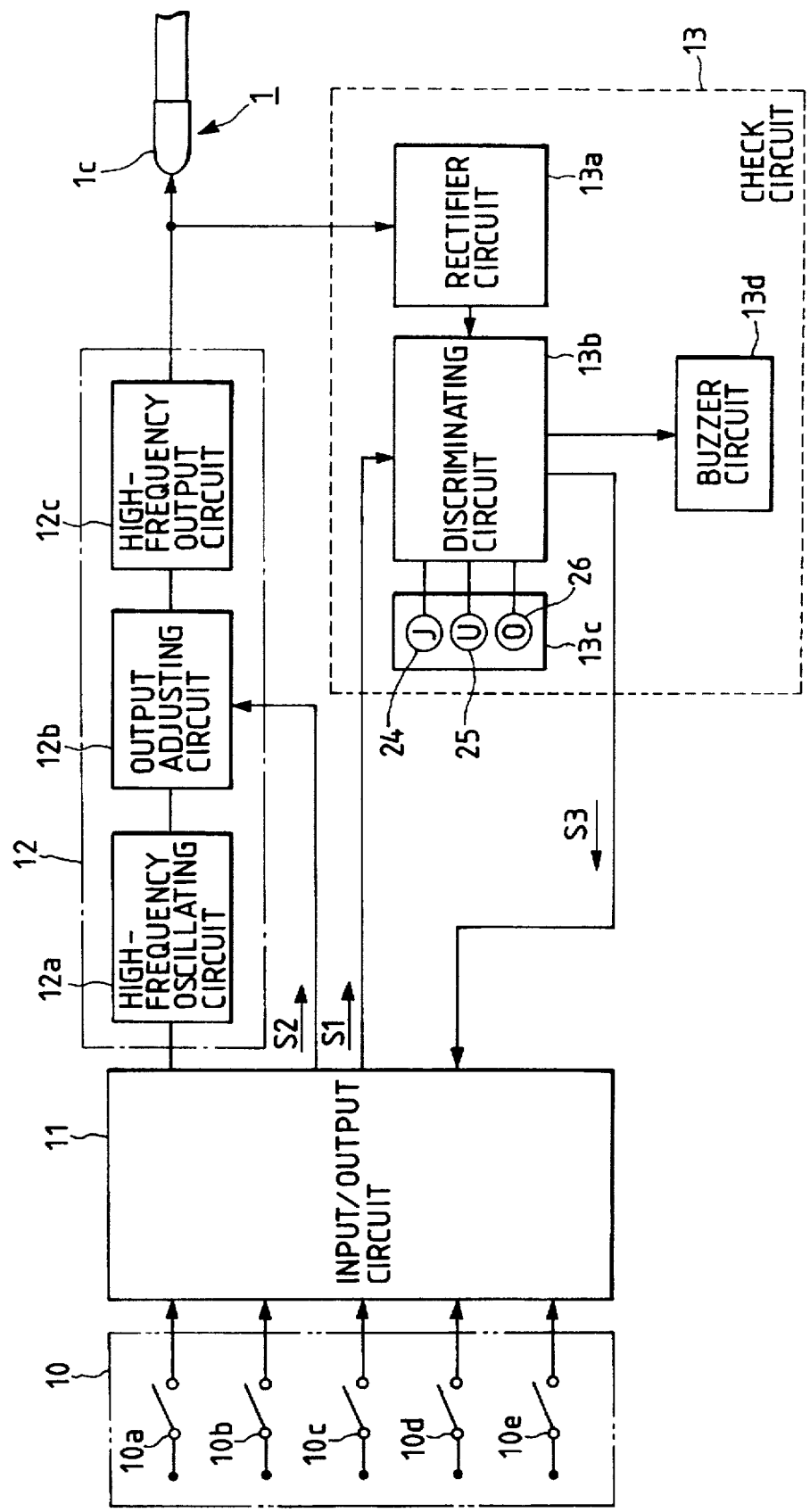
FIG. 1 is a block diagram showing the electrical arrangement of a power unit, which constitutes a preferred embodiment of the invention.

Now, the electrical arrangement of the high-frequency heating power unit 5 will be described with reference to a block diagram of FIG. 1.

The power unit 5 comprises a switch circuit 10, an input/output circuit 11, a high-frequency generating circuit 12, and a check circuit 13.

The switch circuit 10 comprises a check switch 10a, a high-frequency power on switch 10b, a high-frequency power off switch 10c, a reset switch 10d, and a high-frequency fusing output operation switch 10e. The output terminals of those switches 10a through 10e are connected to input terminals of the input/output circuit 11.

The high-frequency generating circuit 12 comprises a high-frequency oscillating circuit 12a, an output adjusting circuit 12b, and a high-frequency output circuit 12c. An output terminal of the input/output circuit 11 is connected to the input terminal of the high-frequency oscillating circuit 12a so that an output signal of the input/output circuit 11 is applied to the high-frequency oscillating circuit 12a. The output terminal of the high-frequency oscillating circuit 12a is connected to the input terminal of the output adjusting circuit 12b, the output terminal of which is connected to the input terminal of the high-frequency output circuit. An output terminal of the input/output circuit 11 is connected to the control terminal of the output adjusting circuit 12b.

The high-frequency output circuit 12c, as shown in FIG. 6, is connected to the output terminals 5a and 5b.

The check circuit comprises a rectifier circuit 13a, a discriminating circuit 13b, a display circuit 13c, and a buzzer circuit 13d. The input terminal of the rectifier circuit 13a is connected to the output terminal of the high frequency output circuit 12c.

The arrangement of the check circuit 13 will be described with reference to an electrical circuit diagram of FIG. 7 which mainly indicates the discriminating circuit 13b.

Figure 7:
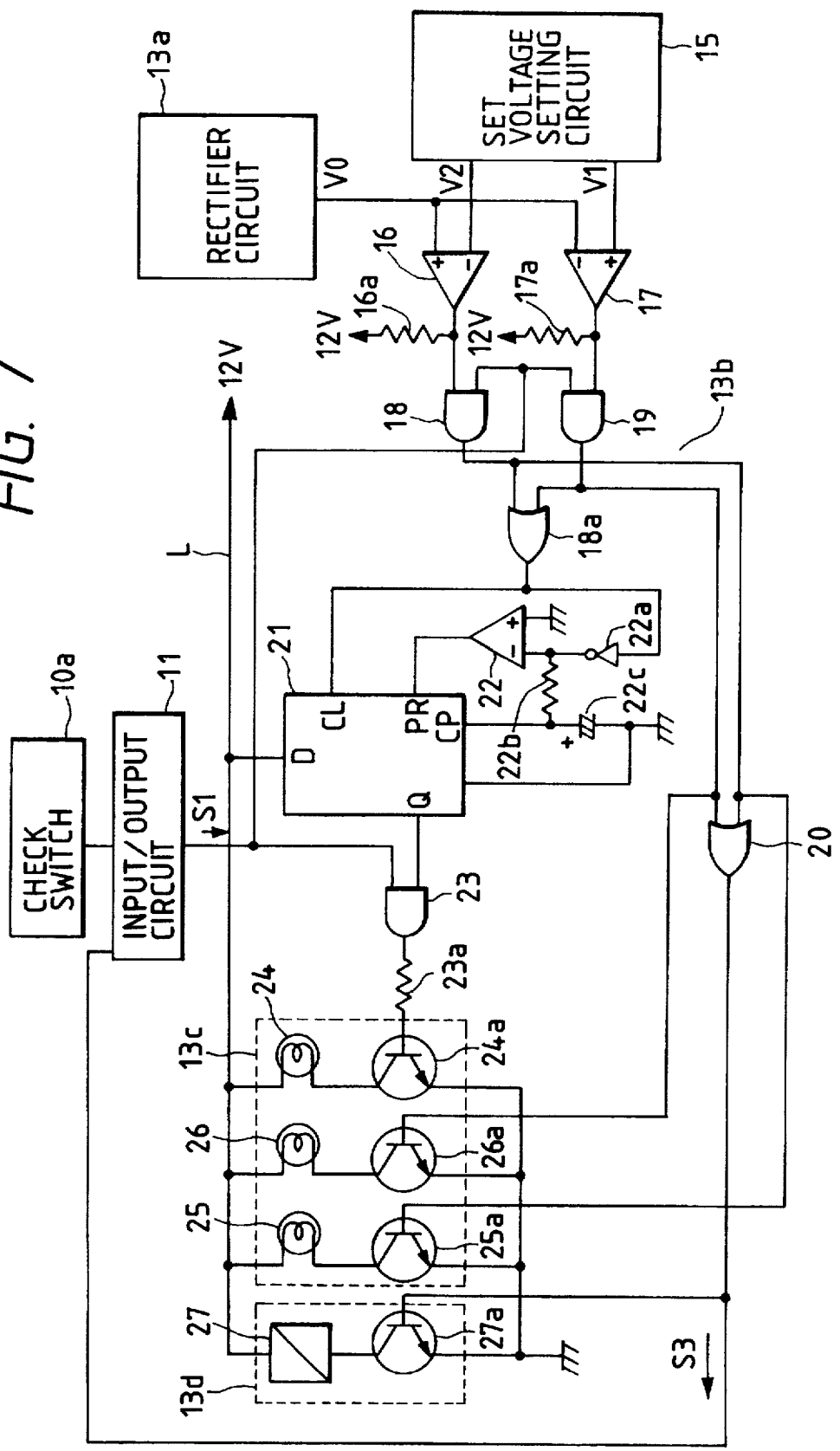
FIG. 7 is a circuit diagram showing various circuits around a discriminating circuit.

In FIG. 7, two output terminals of a set voltage setting circuit 15 are connected to an inversion input terminal of a comparator 16 and a non-inversion input terminal of another comparator 17, respectively, and the output terminals of the rectifier circuit 13a are connected to the non-inversion-input terminal of the comparator 16 and the inversion input terminal of the comparator 17, respectively.

The output terminals of the comparators 16 and 17 are connected respectively through resistors 16a and 17a to a DC power line L. Furthermore, the output terminal of the comparator 16 is connected to one input terminal of an AND gate 18, while the output terminal of the comparators 17 is connected to one input terminal of an AND gage 19. Moreover, the output terminal of the AND gate 18 is connected to one input terminal of an OR gate 20, while the output terminal of the AND gate 19 is connected to the other input terminal of the OR gate 20.

The remaining input terminals of the AND gates 18 and 19 are connected to the output terminal of the input/output circuit 11. The output terminals of the AND gates 18 and 19 are connected through an OR gate 18a to the clear terminal CL of a D-type flip-flop circuit. The output of the OR gate 18a is connected through an inverter circuit 22a to the inversion input terminal of an operational amplifier 22, the output terminal of which is connected to the preset terminal PR of the aforementioned D-type flip-flop circuit 21. In the operational amplifier 22, its non-inversion input terminal is directly grounded, and its inversion input terminal is grounded through a series circuit of a resistor 22b and a capacitor 22c. The common connecting point of the resistor 22b and the capacitor 22c is connected to the clock terminal CP of the D-type flip-flop circuit 21. The data input terminal D of the D-type flip-flop circuit 21 is connected to the DC power line L, and the output terminal Q is connected to one input terminal of an AND gate 23, the other input terminal of which is connected to the output terminal of the input/output circuit 11.

The display circuit 13c includes: informing means, specifically, an adequate state displaying lamp 24, an inadequate state displaying lamp 25, and an excessive state displaying lamp 26, which are connected in series to NPN type transistors 24a, 25a, and 26a, respectively. Those series circuits are parallel-connected between the DC power line L and ground. The base of the transistor 24a is connected through a resistor 23a to the output terminal of the AND gate 23, and the base of the transistor 25a is connected to the output terminal of the AND gate 18, and the base of the transistor 26a is connected to the output terminal of the AND gate 19.

The buzzer circuit 13d comprises informing means, specifically, a buzzer 27 which is connected through an NPN type transistor 27a between the DC power line L and ground. The base of the transistor 27a is connected to the output terminal of the OR gate 20, which is connected to one input terminal of the input/output circuit 11.

The operation of the embodiment thus configured will be described with reference to FIG. 8 as well as FIGS. 1 through 7.

Figure 8:
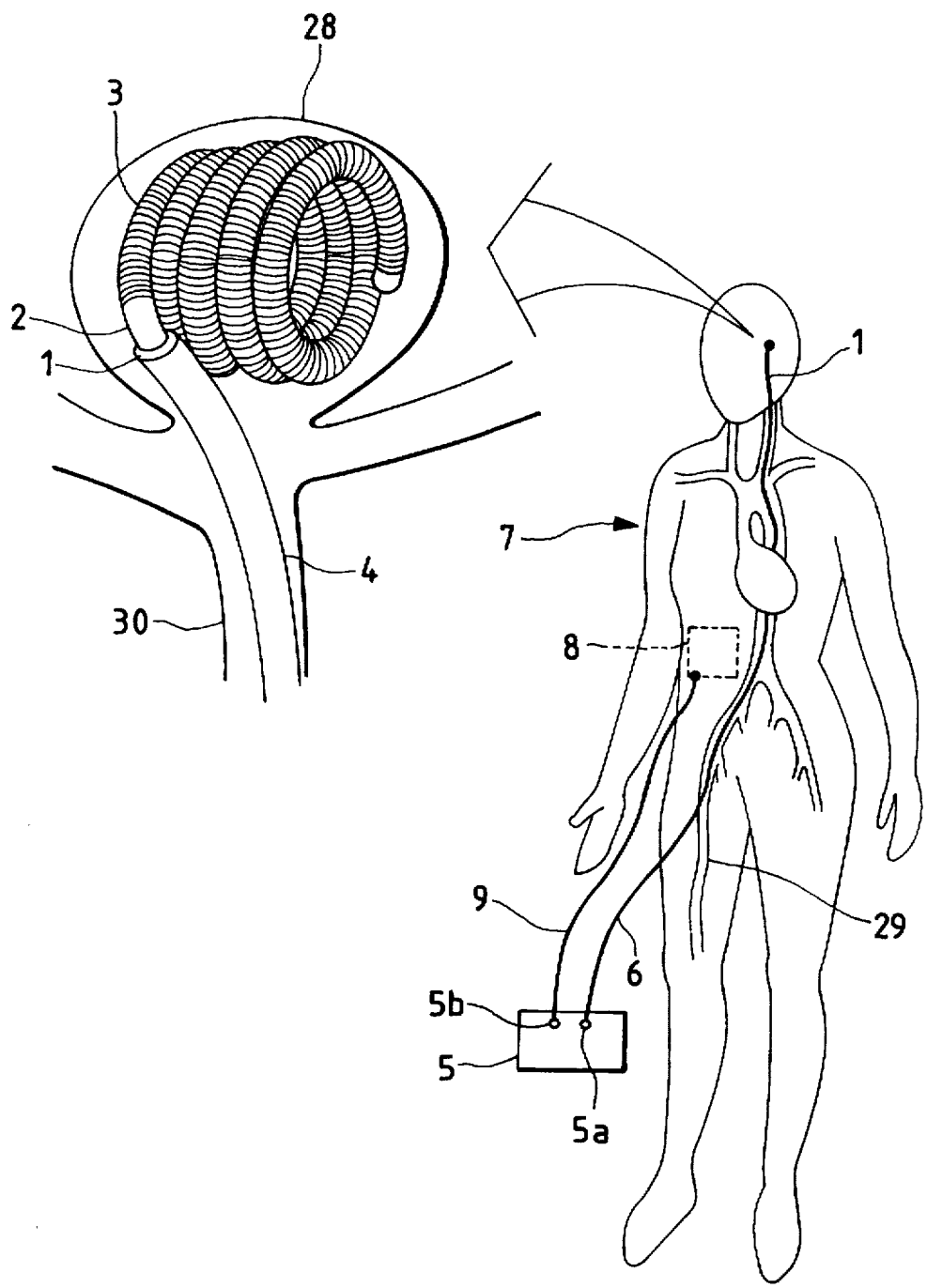
FIG. 8 is an explanatory diagram showing the use of the power unit of the invention.

As shown in FIG. 8, the body grounding board 8 is set in contact with the back of the patient's body, or at another place on the patient's body and the lead wire connected to the body grounding board 8 is connected to the terminal 5b of the high-frequency heating power unit 5. Under this condition, the guide wire 1 is allowed to reach the affected part 18 where the cerebral aneurysm has been formed in this case. The guide wire 1 inserted into the catheter 4 is inserted into the blood vessels from a predetermined anesthetized point on the patient's body. In this case, the guide wire is inserted into the femoral artery 29 from a needled part thereof. While watching the X-ray fluoroscopic image, the guide wire is led to the cranial artery 30, and the implanted device 3 is led to the affected part 28 where the cerebral aneurysm has been formed.

After the implanted device 3 has been led to the affected part 28, the electrode connecting portion 1c of the guide wire 1 is connected through the lead wire 6 to the output terminal 5a of the high-frequency heating power unit 5. Thereafter, the high-frequency power on switch 10b of the power unit 5 is turned on, and the check switch 10a is turned to determine whether or not the end of the guide wire 1 is outside the catheter 4. As a result, a high-level check start signal S1 is applied through the input/output circuit 11 to the check circuit 13. The high-level check start signal S1 is applied to the input terminals of the AND gates 18, 19 and 23 in FIG. 7.

Furthermore, when the check switch 10a is turned on, the high frequency oscillating circuit 12a, the output adjusting circuit 12b, and the high-frequency output circuit 12c operates. A measuring high-frequency voltage, which is too low to fuse the joint member 2, is then allowed to flow through the lead wires 6 and 9 between the guide wire 1 and the body grounding board 8.

The check circuit 13 is to determine whether or not, when the high-frequency measuring voltage lower than the aforementioned high-frequency fusing voltage is applied between the guide wire 1 and the body grounding board 8, the end of the guide wire is located outside the catheter. The following facts have been found through experiments. When the joint member 2 is located in a positional range from the position where it is in alignment with the end of the catheter 4 to the position where it is 1 mm ahead of the end the catheter (the adequate state shown in FIG. 4). When the joint member 2 is positioned where it can be suitably fused, the impedance of the circuit A, consisting of the lead wire 6, the guide wire 1, the patient's body 7, the body grounding board 8, and the lead wire 9, is in a range of from 150 to 600 Ω. When the joint member 2 is more than 1 mm ahead of the end of the catheter 4 (the excessive state shown in FIG. 5), the impedance of the circuit A is 150 Ω or lower. When the joint member 2 is located inside the catheter 4 (the inadequate state shown in FIG. 3), the impedance of the circuit A is over 600 Ω. Thus, in correspondence to the impedances of those various cases, different voltages are provided in the circuit A. And, as shown in an explanatory diagram of FIG. 6, with the aid of the rectifier circuit 13a, a detection voltage V0 is obtained in correspondence to the impedance of the circuit A. The voltage V0 thus obtained corresponds to an impedance measurement value in the high-frequency heating power unit according to the invention.

The set voltage setting circuit 15 applies setting voltage signals to the comparators 16 and 17. In this case, an upper limit set voltage V2 corresponding to 600 Ω is applied to the comparator 16, while a lower limit set voltage VI corresponding to 150 Ω is applied to the comparator 17. Those voltages are compared with the detection voltage VO. The detection voltage V0 provided by the rectifier circuit 13a is compared with the upper and lower limit voltages V2 and VI, to determine the location of the end of the guide wire 1.

The signals will now be described, with reference to FIG. 7, which flow when the joint member 2 is positioned where it is to be fused (the adequate state), or located outside the catheter 4 (the excessive state), or located inside the catheter 4 (the inadequate state).

When the joint member is at the fusing position (as shown in FIG. 4), VI≦VO≦V2, and, therefore, the output of the comparator 16 is a low-level "0" signal, and the output of the comparator 16 is also a low-level "0" signal. Those outputs of the comparators 16 and 17 are applied to the first input terminals of the AND gates 18 and 19, respectively. The high-level start signal S1 is applied to the second input terminals of those AND gates 18 and 19 at all times, and therefore the outputs of the AND gates 18 and 19 are at low level "0". Since the outputs of the AND gates 18 and 19 are at low level "0" the output of the OR gate 18a is also at low level "0", the output of the invert circuit 22a is at high-level "1". The input to the clock terminal CP of the D-type flip-flop circuit 21 is raised to high level "1" after being time-delayed by the resistor 22b and the capacitor 22c. And in the D-type flip-flop circuit 21, an input to the data terminal D is at high level "1" (12V), in response to the rise of the high level "1" signal applied to the clock terminal CK, the output of the output terminal is raised to high level "1". This high level "1" signal is applied to the first input terminal of the AND gate 23, to the second input terminal of which the high level start signal S1 provided by the input/output circuit 11 is applied. Hence, the output of the AND gate 23 is raised to high level "1", so that the transistor 24a is rendered conductive (on), and the adequate state displaying lamp 24 is turned on.

When, with the joint member 2 at the fusing position, the reset switch 10d is turned on, the outputting of the start signal S1 by the input/output circuit 11 is stopped (or the start signal S1 is set to low level), so that the check circuit 13 is turned off. After it has been confirmed through the X-ray fluoroscopic image that the radiopaque marker 1b is substantially in alignment with the first radiopaque mark 4a of the catheter 4 (as shown in FIG. 4), the operating switch 10e is turned on. As a result, the input/output circuit 11 outputs high level control signal S2, which is applied to the control terminal of the output adjusting circuit 12b of the high frequency generating circuit 12. In response to the control signal S2, the output adjusting circuit 12b outputs a fusing high frequency voltage so that a high frequency current flows to fuse the joint member 2, with the Joule heat, which is located between the guide wire 1 and the implanted device 2. The output adjusting circuit 12b may be so modified that it can be manually operated to increase the high-frequency fusing voltage stepwise. Thus, the implanted device is detached from tee guide wire 1. Thereafter, the blood around the implanted device left in the affected part 28 where the cerebral aneurysm has been formed (hereinafter referred to as "a detained member", when applicable) cannot flow smoothly, thus forming a large thrombus. Thereafter, the high frequency power off switch 10c is operated to turn off the high frequency generating circuit 12.

The case where the joint member 2 is located inside the catheter 4 (as shown in FIG. 3) will now be described.

In this case, the impedance of the circuit A is increased, and the detection voltage VO from the rectifier circuit 13a is higher than V2 (VO>V2). Hence, the comparator 16 outputs a high level "1" signal. The "1" signal is applied to the first input terminal of the AND gate 18, to the second input terminal of which the high level start Signal 51 is applied. Therefore, the output of the AND gate 18 is raised to "1" (a high level). As a result, the transistor 25 is rendered conductive (on), and the inadequate state displaying lamp 25 is turned on. On the other hand, the "1" signal of the AND gate 18 is applied through the OR gate 18a to the clear terminal CL of the D-type flip-flop circuit 21, so that the D-type flip-flop circuit is cleared in response to the rise of the signal "1", and the output terminal Q provides a low level signal which is applied to the AND gate 23. When the joint member 2 is located inside the catheter 4, the adequate state displaying lamp 24 is not turned on. The comparator 17 outputs a "0" level signal, and therefore, the output of the AND gate 19 is set to "0" level, and the excessive state displaying lamp is not turned on either.

The output "1" signal from the AND gate 18 is applied to the OR gate 20, and therefore, the output of the gate 20 is raised to high level "1". As a result, the transistor 27a is turned on, and the buzzer 27 is operated. On the other hand, the output "1" signal of the OR gate 20 is applied, as a high-frequency fusing output inhibition signal 53, to the input/output circuit 1. In response to the inhibition signal S3, the input/output circuit 2 inhibits the outputting of the control signal S2 even if the operating switch 10e is turned on. That is, the input/output circuit functions as inhibiting means for preventing the high-frequency generating circuit 12 from outputting the fusing high frequency voltage.

The case where it is determined that the joint member 2 is located outside the catheter 4 (as shown in FIG. 5), will now be described.

In this case, the impedance of the circuit A is lower than 150 Ω, and the detection voltage VO from the rectifier circuit 13a is lower than V1 (VO<V1). Therefore, the comparator 17 provides a high-level "1" signal. The high level "1" signal is applied to the first input terminal of the AND gate 19, to the second input terminal of which the high-level start signal S1 is applied. As a result, the output of the AND gate 19 is raised to high-level "1", so that the transistor 26a is rendered conductive (on), to turn on the excessive state displaying lamp 26. On the other hand, the high level signal of the AND gate 19 is applied through the OR gate 18a to the clear terminal CL of the D-type flip-flop circuit 21, so that the output terminal Q provides a low level signal which is applied to the AND gate 23. Hence, when the joint member 2 is located outside the catheter 4, the adequate state displaying lamp 24 is not turned on. The comparator 16 outputs a low-level "0" signal. Therefore, the output of the AND gate 18 is set to low level "0", and the inadequate state displaying lamp is not turned on either.

The output "1" signal of the AND gate 19 is applied to the OR gate 20. That is, it is applied through the OR gate 20 to the buzzer circuit 13d. Hence, when the guide wire 1 is located outside the catheter, the buzzer 27 is operated. On the other hand, the output "1" of the OR gate 20 is applied, as the high-frequency fusing output inhibition signal S3, to the input/output circuit 11, so that, even if the operating switch 10e is turned on, the input/output circuit 11 will not output the control signal S2.

As is apparent from the above description, in the high-frequency power unit 5, the measuring high-frequency voltage is applied between the guide wire 1 and the body grounding board 8 through the lead wires 6 and 9, and the impedance of the circuit A made up of the lead wire 6, the guide wire 1, the patient's body 7, the body grounding board 8, and the lead wire 9 is measured by using the DC voltage which is obtained by converting the voltage of the circuit A with the aid of the rectifier circuit 13a. Hence, in detaching the implanted device 3 from the guide wire 1 which has been inserted into the affected part where the cerebral aneurysm has been formed, it can be readily determined without reference to the X-ray fluoroscopic image whether or not the joint member 2 is at the fusing position where the joint member 2 is outside the catheter 4 and is slightly ahead of the catheter 4.

In this operation, the high-frequency measuring voltage is lower than the fusing high-frequency voltage used to fuse the joint member 2. Hence, the difficulty will never occur that during the measurement of the impedance the joint member is fused.

When it is determined that the detection voltage corresponding to the impedance of the circuit A is in the set voltage range of from the lower set voltage V1 and the upper set voltage V2, the adequate state displaying lamp 24 is turned on. In addition, when it is determined that the detection voltage is out of the range of allowable voltages more specifically, when the detection voltage is higher, then the inadequate state displaying lamp 25 is turned on. When it is determined that the detection voltage is lower than the range of allowable voltages, the excessive state displaying lamp 26 is turned on. Hence, it can be determined from the displaying lamps turned on whether the joint member 2 is located at the fusing position, or whether it is located inside the catheter, or whether it is located excessively outside the catheter.

If the detection voltage Vo is not in the range of allowable voltages, then the buzzer 27 is operated. Hence, the operator (or user) is informed of the fact that the joint member 2 is not at the fusing position; and it should not be fused. In this case, even if the operating switch 10e has been turned on, the high-frequency generating circuit 12 produces no high-frequency fusing voltage. Hence, even if, in the case where the joint member 2 is not at the fusing position, the operating switch 10e is operated by mistake, the joint member 2 will not be fused.

The preferred embodiment of the invention has been described with reference to the treatment of the cerebral aneurysm. However, the invention is not limited thereto or thereby. That is, the technical concept of the invention is applicable to all medical treatments in which the implanted device is detached from the guide wire.

Furthermore, the invention is not limited to the embodiment described with reference to the accompanying drawings. It may be changed and modified for instance as follows:

The buzzer 27 may be so modified that it is operated when the detection voltage V0 is within the range of allowable voltages. In addition, informing means may be formed by using sound producing units instead of the lamps 24, 25 and 26 and the buzzer 27.

What is claimed is:

1. A high-frequency heating power device comprising:
   a conductive leading member inserted into a catheter adapted to be inserted through a patient's body;
   a grounding plate adapted to be set in contact with the patient's body;
   a high-frequency heating power member for applying a high-frequency heating voltage to said conductive leading member through a lead wire to heat a tip portion of said conductive leading member, said high-frequency heating power member being electrically arranged between said conductive leading member and the grounding plate;
   an impedance measuring for applying a high-frequency measuring voltage lower than said high-frequency heating voltage between said conductive leading member and said grounding plate, to measure an impedance of a circuit which is made up of said lead wire, said conductive leading member, said patient's body, and said grounding plate; and
   an implanted device connected through a joint member to the tip portion of said conductive leading member, said joint member capable of being fused by application of said high-frequency heating voltage.

2. The high-frequency heating power device as claimed in claim 1, further comprising:
   comparison means for determining whether or not an impedance value measured by said impedance measuring member is in a predetermined allowable range, and for outputting a signal when said impedance value is out of said predetermined allowable range.

3. The high-frequency power device as claimed in claim 2, further comprising:
   an informing member operated according to a signal provided by said comparison means.

4. The high-frequency heating power device of claim 1, wherein the joint member comprises a thermally fusible material.

5. The high-frequency heating power device of claim 4, wherein the joint member comprises polyvinyl alcohol (PVA).

6. A high-frequency heating power device comprising:
   a conductive leading member inserted into a catheter adapted to be inserted through a patient's body;
   a grounding plate adapted to be set in contact with the patient's body;
   a high-frequency heating power member for applying a high-frequency heating voltage to said conductive leading member through a lead wire to heat a tip portion of said conductive leading member, said high-frequency heating power member being electrically arranged between said conductive leading member and the grounding plate;

an impedance measuring member for applying a high-frequency measuring voltage lower than said high-frequency heating voltage between said conductive leading member and said grounding plate, to measure an impedance of a circuit which is made up of said lead wire, said conductive leading member, said patient's body, and said grounding plate; and inhibiting means for inhibiting the application of said high-frequency heating voltage which is used for fusing a joint member, when an impedance value measured by said impedance measuring member is out of a predetermined allowable range.

7. The high-frequency heating power device as claimed in claim 6, further comprising:

comparison means for determining whether or not an impedance value measured by said impedance measuring member is in a predetermined allowable range, and for outputting a signal when said impedance value is out of said predetermined allowable range.

8. The high-frequency heating power device as claimed in claim 7, further comprising:

an informing member operated according to a signal provided by said comparison means.

9. The high-frequency heating power device as claimed in claim 6, further comprising:

an implanted device connected through a joint member to the tip portion of said conductive leading member, said joint member capable of being fused by application of said high-frequency heating voltage.

10. The high-frequency power device as claimed in claim 9, further comprising:

comparison means for determining whether or not an impedance value measured by said impedance measuring member is in said predetermined allowable range, and for outputting a signal when said impedance value is out of said predetermined allowable range.

11. The high-frequency power device as claimed in claim 10, further comprising:

an informing member operated according to a signal provided by said comparison means.

12. The high-frequency heating power device of claim 9, wherein the joint member comprises a thermally fusible material.

13. The high-frequency heating power device of claim 12, wherein the joint member comprises polyvinyl alcohol (PVA).

* * * * *